US011081017B2

(12) United States Patent
Isozu

(10) Patent No.: US 11,081,017 B2
(45) Date of Patent: Aug. 3, 2021

(54) INFORMATION PROCESSING APPARATUS, INFORMATION PROCESSING METHOD, AND PROGRAM

(71) Applicant: SONY CORPORATION, Tokyo (JP)

(72) Inventor: Masaaki Isozu, Tokyo (JP)

(73) Assignee: SONY CORPORATION, Tokyo (JP)

( * ) Notice: Subject to any disclaimer, the term of this patent is extended or adjusted under 35 U.S.C. 154(b) by 357 days.

(21) Appl. No.: 15/769,149

(22) PCT Filed: Oct. 12, 2016

(86) PCT No.: PCT/JP2016/080200
§ 371 (c)(1),
(2) Date: Apr. 18, 2018

(87) PCT Pub. No.: WO2017/090329
PCT Pub. Date: Jun. 1, 2017

(65) Prior Publication Data
US 2018/0301051 A1 Oct. 18, 2018

(30) Foreign Application Priority Data
Nov. 24, 2015 (JP) ............................ JP2015-228407

(51) Int. Cl.
*G09B 7/02* (2006.01)
*G06Q 50/20* (2012.01)
*H04L 9/06* (2006.01)
*H04L 29/08* (2006.01)
*G06F 13/00* (2006.01)
(Continued)

(52) U.S. Cl.
CPC ............... *G09B 7/02* (2013.01); *G06F 13/00* (2013.01); *G06Q 40/00* (2013.01); *G06Q 50/20* (2013.01); *G16H 10/00* (2018.01); *H04L 9/0637* (2013.01); *H04L 9/3239* (2013.01); *H04L 63/04* (2013.01); *H04L 63/12* (2013.01);
(Continued)

(58) Field of Classification Search
CPC .......... G06Q 50/20; G06Q 40/00; G09B 7/02; H04L 9/0637; H04L 67/1042
See application file for complete search history.

(56) References Cited

U.S. PATENT DOCUMENTS

2003/0069883 A1 4/2003 Etoh et al.
2005/0075900 A1 4/2005 Arguimbau, III
(Continued)

FOREIGN PATENT DOCUMENTS

CN 101340300 A 1/2009
CN 102497847 A 6/2012
(Continued)

OTHER PUBLICATIONS

Fuchita, Y., "Innovation of block chain and financial transaction", Nomura Capital Markets Quarterly, vol. 19-2, Nov. 1, 2015, 63 pages (with English translation).
(Continued)

*Primary Examiner* — Eddy Saint-Vil
(74) *Attorney, Agent, or Firm* — Oblon, McClelland, Maier & Neustadt, L.L.P.

(57) ABSTRACT

Provided is an information processing apparatus including a processing unit configured to evaluate an evaluation target on a basis of target data regarding the evaluation target acquired from blockchain data circulated on a peer-to-peer network.

11 Claims, 13 Drawing Sheets

(51) Int. Cl.

| | |
|---|---|
| ***H04L 29/06*** | (2006.01) |
| ***G06Q 40/00*** | (2012.01) |
| ***H04L 9/32*** | (2006.01) |
| ***G16H 10/00*** | (2018.01) |
| *G16H 10/60* | (2018.01) |

(52) U.S. Cl.
CPC ......... *H04L 67/1042* (2013.01); *G16H 10/60* (2018.01); *H04L 9/3247* (2013.01); *H04L 2209/38* (2013.01)

(56) References Cited

U.S. PATENT DOCUMENTS

| | | | | |
|---|---|---|---|---|
| 2011/0171622 | A1 | 7/2011 | Lippert et al. | |
| 2014/0214709 | A1 | 7/2014 | Greaney | |
| 2015/0332283 | A1 | 11/2015 | Witchey | |
| 2016/0055236 | A1 * | 2/2016 | Frank | G06Q 30/02 707/748 |
| 2016/0098723 | A1 * | 4/2016 | Feeney | G06Q 20/065 705/75 |

FOREIGN PATENT DOCUMENTS

| | | | |
|---|---|---|---|
| CN | 104823210 | A | 8/2015 |
| EP | 1 018 717 | A2 | 7/2000 |
| JP | 2003-187053 | A | 7/2003 |
| JP | 2012-256008 | A | 12/2012 |
| JP | 2014-48909 | A | 3/2014 |
| WO | 97/42615 | A1 | 11/1997 |
| WO | WO 2015/175722 | A1 | 11/2015 |

OTHER PUBLICATIONS

International Search Report dated Dec. 13, 2016 in PCT/JP2016/080200 filed Oct. 12, 2016.
Office Action dated Jan. 16, 2020 in corresponding Japanese Patent Application No. 2017-552308 (with English Translation), 16 pages.
Extended European Search Report dated Oct. 8, 2018 in Patent Application No. 16868278.9, 7 pages.
Melanie Swan, "Blockchain: Blueprint for a New Economy" O'Reilly, XP055279098, Feb. 8, 2015, 142 pages.

* cited by examiner

FIG. 3

| TRANSACTION ID | TRANSMISSION SIDE | RECEPTION SIDE | SCORES | CONTENTS ID | TIME |
|---|---|---|---|---|---|
| 001ade71b8 | TEST ORGANIZATION A | USER B | 10 | 3dc66fa900 | 2015/10/01 10:08:32 |
| 001ade71b9 | TEST ORGANIZATION A | USER B | 15 | 3dc66fa901 | 2015/10/01 10:09:10 |
| 001ade71b0 | TEST ORGANIZATION A | USER B | 5 | 3dc66fa902 | 2015/10/01 10:12:06 |
| 001ade71a1 | TEST ORGANIZATION A | USER B | 0 | 3dc66fa903 | 2015/10/01 10:15:44 |
| 01bc264dcf | USER B | EVALUATION ORGANIZATION C | 820 | 08aee076f1 | 2015/12/10 09:10:11 |
| 01bc264dd0 | USER B | EVALUATION ORGANIZATION D | 820 | 19b22eff2a | 2015/12/10 09:10:12 |
| ⋮ | ⋮ | ⋮ | ⋮ | ⋮ | ⋮ |

STATE IN WHICH USER B TAKES TEST

USER B SUBMITS TEST RESULT TO EVALUATION ORGANIZATION

FIG. 8

| TRANSACTION ID | TRANSMISSION SIDE | RECEPTION SIDE | SCORES | CONTENTS ID | TIME |
|---|---|---|---|---|---|
| 001ade71b8 | T | U1 | 10 | 3dc66fa900 | |
| 001ade71b9 | T | U1 | 15 | 3dc66fa901 | |
| 001ade71b0 | T | U2 | 5 | 3dc66fa902 | |
| 001ade71a1 | T | U2 | 0 | 3dc66fa903 | |
| 01bc264dcf | U3 | EA | 820 | 08aee076f1 | |
| 01bc264dd0 | U3 | EB | 820 | 19b22eff2a | |

| TRANSACTION ID | TRANSMISSION SIDE | RECEPTION SIDE | SCORES | CONTENTS ID | TIME |
|---|---|---|---|---|---|
| 001ade71b8 | T | U1 | 10 | 3dc66fa900 | |
| 001ade71b9 | T | U1 | 15 | 3dc66fa901 | |
| 001ade71b0 | T | U2 | 5 | 3dc66fa902 | |
| 001ade71a1 | T | U2 | 0 | 3dc66fa903 | |
| 01bc264dcf | U3 | EA | 820 | 08aee076f1 | |
| 01bc264dd0 | U3 | EB | 820 | 19b22eff2a | |

- ANSWER CONTENTS OF QUESTIONS
- CORRECT OR INCORRECT ANSWERS TO QUESTIONS
- ANSWER TIME OF QUESTIONS
- SCORES OF QUESTIONS
- MOTION OF VISUAL LINE OF EXAMINEE
- CHANGE IN ATTITUDE OF EXAMINEE
- HEART RATE OR AMOUNT OF PERSPIRATION OF EXAMINEE
- INPUT SPEED OF KEYBOARD
- MOTION OF POINTER
- SITUATION OF ANOTHER APPLICATION

| TRANSACTION ID | TRANSMISSION SIDE | RECEPTION SIDE | CORRECT /INCORRECT | ANSWER TIME | SCORES (RAW SCORES) |
|---|---|---|---|---|---|
| 001ade71b8 | T | U1 | OK | 55 SECONDS | 20 |
| 001ade71b9 | T | U1 | OK | 30 SECONDS | 10 |
| 001ade71b0 | T | U2 | NG | 10 SECONDS | 0 |
| 001ade71a1 | T | U2 | NG | 50 SECONDS | 0 |

B

| EVALUATION ORGANIZATION X | EVALUATION ORGANIZATION Y | |
|---|---|---|
| 20 | 20 | |
| 10 | 15 | P |
| 0 | 0 | |
| 0 | 5 | Q |

INFORMATION PROCESSING APPARATUS, INFORMATION PROCESSING METHOD, AND PROGRAM

TECHNICAL FIELD

The present disclosure relates to an information processing apparatus, an information processing method, and a program.

BACKGROUND ART

Technologies for managing evaluation information provided from evaluators via networks have been developed. As a technology for managing evaluation information provided from an evaluator via a network in a server, for example, a technology disclosed in the following Patent Literature 1 can be exemplified.

CITATION LIST

Patent Literature

Patent Literature 1: JP 2003-187053A

DISCLOSURE OF INVENTION

Technical Problem

For example, when a case in which an evaluation target is evaluated, such as a case in which a test result of an evaluation target user is evaluated or a case in which a learning result of the evaluation target user is evaluated, is assumed, whether the test result or the learning result of the user is good changes depending on a criterion of each evaluator (or an evaluation organization; hereinafter the same applies below) of a university, a company, or the like in some cases. Further, when each of the foregoing cases is assumed, an evaluator and a maintainer (or a maintaining organization) that has the test result of the evaluation target user or the learning result of the evaluation target user are different in some cases.

Here, as a method of realizing evaluation of an evaluation target by a criterion of each evaluator, for example, "a method in which target data regarding an evaluation target is maintained on a network, each evaluator acquires the target data regarding the evaluation target from the network, and the evaluation target is evaluated by a criterion of each evaluator" is considered. However, there is no "structure in which each evaluator can acquire target data regarding an evaluation target maintained on a network and evaluate the evaluation target by a criterion of each evaluator."

The present disclosure proposes a novel and improved information processing apparatus, a novel and improved information processing method, and a novel and improved program capable of realizing evaluation of an evaluation target based on target data regarding the evaluation target maintained on a network.

Solution to Problem

According to the present disclosure, there is provided an information processing apparatus including a processing unit configured to evaluate an evaluation target on a basis of target data regarding the evaluation target acquired from blockchain data circulated on a peer-to-peer network.

In addition, according to the present disclosure, there is provided an information processing method to be performed by an information processing apparatus, the information processing method including a step of evaluating an evaluation target on a basis of target data regarding the evaluation target acquired from blockchain data circulated on a peer-to-peer network.

In addition, according to the present disclosure, there is provided a program causing a computer to execute a function of evaluating an evaluation target on a basis of target data regarding the evaluation target acquired from blockchain data circulated on a peer-to-peer network.

Advantageous Effects of Invention

According to the present disclosure, it is possible to realize evaluation of an evaluation target based on target data regarding the evaluation target maintained on a network.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is an explanatory diagram illustrating an example of a use case to which the information processing method according to the embodiment is applied.

FIG. 8 is an explanatory diagram illustrating an example of a use case to which the information processing method according to the embodiment is applied.

FIG. 10 is an explanatory diagram illustrating an example of a use case to which the information processing method according to the embodiment is applied.

FIG. 11 is an explanatory diagram illustrating an example of a use case to which the information processing method according to the embodiment is applied.

MODE(S) FOR CARRYING OUT THE INVENTION

Figure 1:
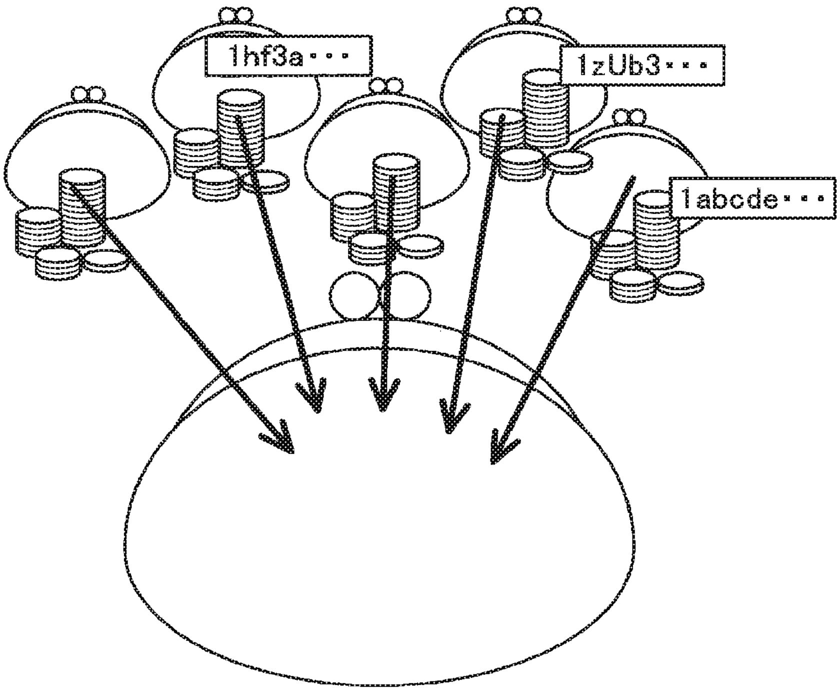
FIG. 1 is an explanatory diagram illustrating an overview of an information processing method according to an embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, in the following description, description will be provided in the following order.

1. Information processing method according to the present embodiment
2. Information processing apparatus according to the present embodiment
3. Program according to the present embodiment (Information Processing Method According to the Present Embodiment)

First, an information processing method according to an embodiment will be described. Hereinafter, a case in which a process related to the information processing method according to the embodiment is performed by an information processing apparatus according to the embodiment will be exemplified.

[1] Method of Acquiring Data in Information Processing Method According to Embodiment As described above, as a method of realizing evaluation of an evaluation target by a criterion of each evaluator, for example, "a method in which target data regarding an evaluation target is maintained on a network, each evaluator acquires the target data regarding the evaluation target from the network, and the evaluation target is evaluated by a criterion of each evaluator" is considered.

Here, when the target data regarding the evaluation target is altered, a legitimate evaluation result may not be expected to be obtained. For this reason, the target data of the evaluation target is preferably maintained on the network, for example, in a form in which the target data is not altered (or a form in which an alternation possibility is low). Note that the target data according to the embodiment will be described later.

Accordingly, first a data acquisition method in the information processing method according to the embodiment will be described.

In the information processing method according to the embodiment, for example, "retention of target data regarding an evaluation target on a network in an unaltered form" is realized by using blockchain data circulated in a peer-to-peer network. The peer-to-peer network is also referred to as a peer-to-peer distributed file system in some cases. Hereinafter, the peer-to-peer network is referred to as a "P2P network" in some cases.

Here, the blockchain data according to the embodiment is data in which a plurality of blocks are connected and included like chains. In each block, one or two or more pieces of target data can be stored as a transaction.

As the blockchain data according to the embodiment, for example, blockchain data used to exchange data of virtual currency such as Bitcoin can be exemplified. In the blockchain data used to exchange data of virtual currency, for example, alternation is prevented by data called nonce, which is used to prevent camouflage in authentication in which a hash is used. As the nonce, for example, data indicating a character string, a digit string, or a combination thereof can be exemplified. Further, in the blockchain data used to exchange data of Bitcoin, data of each transaction is not encrypted and electronic signature in which a cryptographic key is used is assigned, and thus the data of each transaction is made public. On the other hand, for example, there is a technology for maintaining a digital asset on a blockchain of Bitcoin as in Colored Coin. In this case, a design can be realized such that only a specific apparatus that possesses a corresponding cryptographic key (an apparatus capable of decrypting encrypted data) can ascertain content of data on a blockchain.

In a case in which the information processing method according to the embodiment is used, for example, a side chain technology can be used to include target data regarding an evaluation target in blockchain data used to exchange data of existing virtual currency, such as blockchain data of Bitcoin. That is, in the information processing method according to the embodiment, for example, a network of a network formed by unspecified participants (so-called "permissionless system", such as networks related to Bitcoin, can be used.

Further, a network in which the information processing method according to the embodiment can be used is not limited to the foregoing example.

For example, in the information processing method according to the embodiment, a network (a network of a so-called "permissioned system") formed by only authenticated participants (trustworthy participants), such as Private Pools of HyperLedger, can also be used. By using the network formed by only the participants authenticated in the foregoing way, it is possible to further improve reliability of data which is on a network than in a case in which a network formed by unspecified participants is used. Further, a service of a permissioned system can also be designed on a network of a permissionless system. In a case in which a blockchain technology is ascertained as a distributed ledger, for example, centralized setting of a manager capable of performing writing on a ledger or whether to motivate another person to provide a resource for management of a decentralized management ledger can be flexibly selected in accordance with architecture design of a service.

Further, a network in which the information processing method according to the embodiment is used is not limited to the foregoing existing networks used for other purposes and may be a peer-to-peer network in which blockchain data used in only the information processing method according to the embodiment is circulated.

Here, in a case in which blockchain data is used, in order to generate a new block, a process using calculation resources called mining is necessary. Accordingly, in a case in which a peer-to-peer network in which blockchain data used only in the information processing method according to the embodiment is circulated is used, a reward may be given to a person who performs generation of a block. A reward in the case in which a peer-to-peer network in which blockchain data used in only the information processing method according to the embodiment is circulated can be realized by a special transaction called a coin base in, for example, a peer-to-peer network in which existing block chain data is circulated. Further, a reward in the case in which a peer-to-peer network in which blockchain data used in only the information processing method according to the embodiment is circulated may be, for example, a reward which can be a motivation for generating a block and is given in accordance with any method.

Further, the information processing method according to the embodiment is not limited to the use of the peer-to-peer network in which the blockchain data is circulated. For example, any peer-to-peer network in which confidentiality is guaranteed because of encryption can also be used.

Hereinafter, a process related to the information processing method according to the embodiment will be described mainly exemplifying a case in which an existing peer-to-peer network related to Bitcoin is used.

[2] Process Related to Information Processing Method According to Embodiment

The information processing apparatus according to the embodiment evaluates an evaluation target on the basis of target data regarding the evaluation target acquired from blockchain data circulated in a peer-to-peer network (an evaluation process).

The information processing apparatus according to the embodiment acquires target data corresponding to an evaluation target from blockchain data by performing decryption with a cryptographic key corresponding to the evaluation target. Here, as the cryptographic key corresponding to the evaluation target, for example, a secret key corresponding to a public key used to encrypt the target data can be exemplified. The public key is generated from a secret key of an evaluation target, as will be described below.

The cryptographic key corresponding to the evaluation target is acquired, for example, when an evaluation request including a command to execute the evaluation process and the cryptographic key is acquired. Further, the secret key corresponding to the evaluation target may be recorded on a storage unit (to be described below) or a recording medium such as an external recording medium connected to the information processing apparatus according to the embodiment at the time of applying a request for using an evaluation service through the evaluation process and may be acquired by reading the secret key from the recording medium.

When a case in which an existing peer-to-peer network related to Bitcoin is used is exemplified, an address equivalent to a Bitcoin address is generated from the secret key of a user. Specifically, a public key corresponding to the secret key is generated from the secret key of the user and an address is generated with the generated public key. Accordingly, data designated by the address is not decrypted when there is no secret key corresponding to the public key used to generate the address.

Further, in a case in which an existing peer-to-peer network related to Bitcoin is used, a plurality of addresses can be managed with a wallet as in the structure of Bitcoin.

FIG. 1 is an explanatory diagram illustrating an overview of the information processing method according to the embodiment. Management of the plurality of addresses with the wallet is expressed in, for example, an image in which a plurality of wallets are stored in one wallet, as illustrated in FIG. 1.

In a case in which an existing peer-to-peer network related to Bitcoin is used, target data can be sent from an address to an address as in a case in which Bitcoin is sent.

Further, the information processing apparatus according to the embodiment evaluates the evaluation target in accordance with target data corresponding to the evaluation target and an evaluation index set to correspond to the evaluation target. The evaluation index according to the embodiment may be a fixed evaluation index that is set in advance or may be a variable evaluation index that can be changed through a manipulation of a user or the like of the information processing apparatus according to the embodiment.

When the information processing apparatus according to the embodiment evaluates the evaluation target in accordance with the evaluation index set to correspond to the evaluation target, the information processing apparatus according to the embodiment can evaluate the evaluation target by a set independent criterion. Accordingly, when the information processing apparatus according to the embodiment evaluates the evaluation target in accordance with the evaluation index set to correspond to the evaluation target, evaluation of the evaluation target in accordance with the criterion of each evaluator is realized.

The information processing apparatus according to the embodiment may evaluate the evaluation target on the basis of one piece of target data corresponding to the evaluation target or may also evaluate the evaluation value on the basis of a plurality of pieces of target data corresponding to the evaluation target. Here, by evaluating the plurality of pieces of target data corresponding to the evaluation target, for example, "evaluation of a history of details indicated by the target data corresponding to the evaluation target" or "comprehensive evaluation of content indicated by each of the plurality of pieces of target data corresponding to the evaluation target" is realized.

Further, an example of the evaluation index according to the embodiment and an example of evaluation of the evaluation target in which the evaluation index is used will be described later.

Here, as the evaluation target according to the embodiment, for example, a "person (hereinafter a person who is the evaluation target is referred to as a 'user')," a "company, party, or organization," or an "object" can be exemplified.

Further, as the target data according to the embodiment and the evaluation of the evaluation target using the evaluation index based on the target data, examples described in the following (a) to (c) can be exemplified. Further, it is needless to say that examples of the target data according to the embodiment and the evaluation of the evaluation target based on the target data are not limited to the examples described in the following (a) to (c).

(a) Example of target data related to user (a-1) Data indicating test result

In a case in which the target data is data indicating a test result, the information processing apparatus according to the embodiment evaluates a test result of the user.

As data indicating the test result, for example, one or both of data in which the test result of the user is indicated by a numerical value (hereinafter referred to as "first data") and data in which the test result of the user is indicated by a value other than a numerical value (hereinafter referred to as "second data") can be exemplified. As the first data according to the embodiment, for example, data indicating a score of questions given to the user can be exemplified. Further, as the second data according to the embodiment, for example, one or both of content of answers to the questions and correct and incorrect answers to the questions can be exemplified.

Further, the data indicating the test result may further include data indicating a state in which the user takes a test or an environment in which the user takes the test (hereinafter referred to as "third data" in some cases).

As the third data indicating the state at the time at which the user takes the test, for example, data indicating one or two or more of "an answer time of questions," "a motion of a visual line of the user who is an examinee," "a change of an attitude of the user who is an examinee," "a user state such as a heart rate, an amount of perspiration, a body temperature, a blood oxygen level, or an electrocardiogram of the user who is an examinee," "a manipulation state on a device used for a test such as an input speed of a keyboard or a motion of a pointer," and "application states other than an application related to the test (or a situation of the other applications)" can be exemplified. The third data indicating the state at the time at which the user takes the test is generated by, for example, a server that performs a process related to a test, such as supply of questions to the user or reception of the answers, or a biological sensor mounted on a user who is an examinee.

Further, as the third data indicating the environment in which the user takes the test, for example, one or both of "positional information indicating the position of the user" and "environment information indicating an environment related to the user" can be exemplified. As the positional information, for example, data indicating a detection result of a device capable of specifying the position of a global navigation satellite system (GNSS) device or the like (or data indicating an estimation result of a device capable of estimating the position in accordance with any scheme) can be exemplified. Further, as the environment information, for example, data indicating one or two or more of "data indicating a distance between the user and a device used for the test," "data indicating brightness around the user," "data indicating a temperature around the user," "data indicating atmospheric pressure around the user," and "data indicating humidity around the user" can be exemplified. The environment information is generated by, for example, one or two or more sensors such as a distance sensor and an illuminance sensor. For example, any of the above-described various sensors may be worn by the user or may be included in any device used for the user to take the test. Further, any of the above-described various sensors may be included in, for example, a location corresponding to the test, such as a desk on which the user takes the test.

Further, the third data according to the embodiment may include data indicating the same kind of detection result based on detected data of a plurality of different sensors or devices. As one example of the data indicating the same kind of detection result, "data indicating a change in the attitude of the user estimated from detected data of an attitude sensor (for example, an acceleration sensor and an angular velocity sensor) worn by the user" and "data indicating a change in the attitude of the user estimated from a captured image generated by an imaging device that images the user" can be exemplified.

The information processing apparatus according to the embodiment determines the test result of the user, for example, by determining whether the test result indicated by the data indicating the test result satisfies one or two or more set conditions (examples of the evaluation index). Here, a determination result of the test result of the user is equivalent to a result obtained by evaluating the user.

As one example, the information processing apparatus according to the embodiment evaluates the test result of the user, for example, by comparing the numerical value specified on the basis of the target data with one or two or more set predetermined thresholds.

A threshold process in which the set predetermined thresholds are used is equivalent to a process of determining whether the evaluation index is satisfied. As the predetermined threshold according to the embodiment, for example, a fixed threshold that is set in advance or a variable threshold that can be changed through a manipulation by a user or the like of the information processing apparatus according to the embodiment can be exemplified. Here, for example, in a case in which the target data includes first data in which the test result of the user is indicated by a numerical value, the numerical value specified on the basis of the target data is specified on the basis of the numerical value indicated by the first data.

The information processing apparatus according to the embodiment sets, for example, the numerical value indicated by the first data as the numerical value specified on the basis of the target data.

Further, in a case in which the evaluation target is evaluated using a plurality of pieces of target data, the information processing apparatus according to the embodiment may calculate, for example, a numerical value on the basis of the plurality of pieces of first data and set the calculated numerical value as the numerical value specified on the basis of the target data. As the numerical value calculated on the basis of the plurality of pieces of first data, for example, an addition value of the numerical value indicated by each of the plurality of pieces of first data can be exemplified.

Further, in a case in which the target data includes second data in which the test result of the user is indicated by a value other than a numerical value, the numerical value specified on the basis of the target data may be specified on the basis of the numerical value acquired on the basis of the second data.

The information processing apparatus according to the embodiment acquires a numerical value corresponding to the second data with reference to, for example, a table (or a database; the same applies below) in which content indicated by the second data matches the numerical value. Here, the table is stored in, for example, a recording medium such as a storage unit (to be described below).

Then, the information processing apparatus according to the embodiment sets the acquired numerical value corresponding to the second data to the numerical value specified on the basis of the target data.

Further, in a case in which the evaluation target is evaluated using the plurality of pieces of target data, the information processing apparatus according to the embodiment may calculate, for example, a numerical value on the basis of the plurality of pieces of second data and set the calculated numerical value to the numerical value specified on the basis of the target data. As the numerical value calculated on the basis of the plurality of pieces of second data, for example, an addition value such as a numerical value corresponding to each piece of second data acquired on the basis of each of the plurality of pieces of the second data can be exemplified.

Further, for example, in a case in which the target data includes both the first data and the second data, the numerical value specified on the basis of the target data may be specified on the basis of a numerical value indicated by the first data and a numerical value acquired on the basis of the second data. For example, the information processing apparatus according to the embodiment sets an addition value or the like of the numerical value indicated by the first data and the numerical value corresponding to the second data to a numerical value specified on the basis of the target data.

In a case in which the target data is data indicating a test result, the information processing apparatus according to the embodiment evaluates the test result of the user, for example, by comparing a numerical value specified on the basis of one or both of the first data and the second data included in the target data with the one or two or more set predetermined thresholds, as described above.

Further, the evaluation process in the case in which the target data is the data indicating the test result is not limited to the foregoing example.

For example, in a case in which the target data further includes the third data indicating the state in which the user takes the test or the environment in which the user takes the test, the information processing apparatus according to the embodiment can evaluate the test result of the user further on the basis of the third data. As the process of evaluating the test result of the user on the basis of the third data, for example, one or both of a process described in the following (i) and a process described in the following (ii) can be exemplified.

(i) First Example of Process of Evaluating Test Result of User on Basis of Third Data The information processing apparatus according to the embodiment adjusts the numerical value specified on the basis of the above-described target data on the basis of the third data.

The information processing apparatus according to the embodiment acquires an adjustment value corresponding to the third data with reference to, for example, a table in which content indicated by the third data matches the adjustment value (or a database; the same applies below). Here, the table is stored in, for example, a recording medium such as a storage unit (to be described below). Then, the information processing apparatus according to the embodiment adjusts the numerical value specified on the basis of the above-described data by adding the acquired adjustment value corresponding to the third data to the numerical value specified on the basis of the above-described target data.

Then, when the numerical value specified on the basis of the target data is adjusted, the information processing apparatus according to the embodiment evaluates the test result of the user by comparing the adjusted numerical value with one or two or more predetermined thresholds.

(ii) Second Example of Process of Evaluating Test Result of User on Basis of Third Data In the case in which the target data further includes the third data indicating the state in which the user takes the test or the environment in which the user takes the test, the information processing apparatus according to the embodiment further determines legitimacy of the test result on the basis of the third data.

As one example, in a case in which an answer time of the questions (which is an example of content indicated by the third data) is less than a set threshold (or a case in which the answer time of the questions is equal to or less than the threshold), the information processing apparatus according to the embodiment determines that the test result is not legitimate (or is illegal). Here, as the threshold related to the foregoing determination of the legitimacy of the test result, for example, a fixed threshold that is set in advance, a variable threshold that can be changed through a manipulation by the user or the like of the information processing apparatus according to the embodiment, or a threshold that is set in accordance with a learning result of the answer time of the questions corresponding to the illegitimate test result can be exemplified.

As another example, in a case in which a motion of a visual line of the user who is an examinee (which is an example of the content indicated by the third data) is greater than a set threshold (or a case in which the motion of the visual line of the user is equal to or greater than the threshold), the information processing apparatus according to the embodiment determines that the test result is not legitimate (or is illegal). Here, as the threshold related to the foregoing determination of the legitimacy of the test result, for example, a fixed threshold that is set in advance, a variable threshold that can be changed through a manipulation by the user or the like of the information processing apparatus according to the embodiment, or a threshold that is set in accordance with a learning result of the motion of the visual line of the user corresponding to the illegitimate test result can b exemplified.

As further another example, the information processing apparatus according to the embodiment can determine whether the test result is legitimate, for example, by comparing a change in an attitude of the user estimated from detected data of an attitude sensor worn by the user (which is an example of the content indicated by the third data) with a change in an origination of the user estimated from a captured image generated by an imaging device that images the user (which is another example of the content indicated by the third data). For example, in a case in which a difference between the change in the attitude of the user estimated from the detected data of the attitude sensor worn by the user and the change in the attitude of the user estimated from the captured image generated by the imaging device that images the user is greater than a set threshold (or a case in which the difference is equal to or greater than the threshold), the information processing apparatus according to the embodiment determines that the test result is not legitimate (or is illegal). That is, for example, in a case in which the change in the attitude of the user estimated from the detected data of the attitude sensor worn by the user and the change in the attitude of the user estimated from the captured image generated by the imaging device that images the user considerably deviate from each other, the information processing apparatus according to the embodiment can determine that the test result is not legitimate.

Further, the information processing apparatus according to the embodiment can also determine whether the test result is legitimate, for example, by comparing "content indicated by one or both of environmental information indicating an environment around the user, such as a temperature, humidity, and brightness and positional information acquired from the biological sensor worn by the user who is an examinee (which is an example of the content indicated by the third data)" with "content indicated by one or both of positional information acquired from another sensor and environmental information" (another example of content indicated by the third data). The information processing apparatus according to the embodiment determines that the test result is not legitimate in a case in which the comparison results considerably deviate from each other as in the determination based on the change in the attitude.

The information processing apparatus according to the embodiment can further determine the legitimacy of the test result on the basis of the third data, for example, as described above. Note that it is needless to say that an example of the process related to the determination of the legitimacy of the test result based on the third data is not limited to the foregoing examples.

The information processing apparatus according to the embodiment can evaluate the test result of the user by additionally using the third data, for example, as described in the foregoing (1) and (ii). That is, the third data according to the embodiment can be said to be an example of data additionally used to evaluate the user who is an evaluation target. Hereinafter, data additionally used to evaluate an evaluation target as in the third example according to the embodiment is referred to as "additional data."

In a case in which the target data is data indicating the test result, the information processing apparatus according to the embodiment evaluates the test result of the user, for example, as described above.

Note that as a case in which the target data is data other than the data indicating the test result will described below, the evaluation target can be evaluated by performing a process of one or two or more thresholds or a legitimacy determination process even in a case in which the target data is the data other than the data indicating the test result, as in the case in which the target data indicates the data indicating the test result.

Further, the process of evaluating the evaluation target according to the embodiment is not limited to the threshold process and the legitimacy determination process, and may be any process capable of evaluating the evaluation target.

(a-2) Data Indicating Learning Result

In a case in which the target data is data indicating a learning result, the information processing apparatus according to the embodiment evaluates the learning result.

As the data indicating the learning result, for example, one or both of data indicating academic degrees acquired in a university or the like and data indicating credits in a university or the like can be exemplified.

The information processing apparatus according to the embodiment determines pass or fail of an admission test, an employment entrance test, a scholarship examination, or the like, for example, by determining whether the learning result indicated by the data indicating the learning result satisfies one or two or more set conditions (which are examples of the evaluation index). Here, a determination result of the pass or fail of the admission test or the like is equivalent to a result obtained by evaluating the user.

(a-3) Data Regarding Inspection Result of Health Diagnosis

When the target data is data regarding an inspection result, the information processing apparatus according to the embodiment evaluates the inspection result.

As the data regarding the inspection result, for example, data indicating inspection results of any inspection item such as a height, a weight, and a blood pressure can be exemplified.

The information processing apparatus according to the embodiment determines a health state of the user, for example, by determining whether the inspection result indicated by the data indicating the inspection result satisfies one or two or more set conditions (which are examples of the evaluation index). Here, the determination result of the health state of the user is equivalent to a result obtained by evaluating the user.

As one example, the information processing apparatus according to the embodiment determines the inspection result of the user by comparing a numerical value specified on the basis of data regarding the inspection result (which is an example of the target data) with one or two or more set predetermined threshold, as in the case in which the target data described in the foregoing (a-1) is the data indicating the test result.

Further, for example, in a case in which the target data further includes additional data indicating a state in which the user undergoes an inspection or an environment in which the user undergoes the inspection, the information processing apparatus according to the embodiment can also evaluate the inspection result of the user on the basis of the additional data, as in the case in which the target data described in the foregoing (a-1) is the data indicating the test result.

As the additional data indicating the state in which the user undergoes the inspection, for example, data indicating one or more of "a change in an attitude of the user who is an inspection target" and "another application state other than an application related to the inspection (or a situation of the other application)" can be exemplified. Further, as the additional data indicating the environment in which the user undergoes the inspection, for example, one or both of "positional information indicating the position of the user who is the inspection target" and "environmental information indicating the environment related to the user who is the inspection target" can be exemplified.

As an example of a process based on the additional data in a case in which the target data is data regarding the inspection result, the information processing apparatus according to the embodiment adjusts a numerical value specified on the basis of the data regarding the inspection result (which is an example of the target data) on the basis of the additional data, for example, as in the process described in the foregoing (i). Then, the information processing apparatus according to the embodiment evaluates the inspection result of the user by comparing the adjusted numerical value with one or two or more set predetermined thresholds.

Further, as another example of the process based on the additional data in the case in which the target data is the data regarding the inspection result, the information processing apparatus according to the embodiment further determine the legitimacy of the inspection result of the user on the basis of the additional data, for example, as in the process described in the foregoing (ii).

Further, the information processing apparatus according to the embodiment can also perform both a process related to the adjustment of the numerical value based on the additional data and a process related to the determination of the legitimacy of the inspection result based on the additional data.

Note that it is needless to say that an example of the target data in a case in which the evaluation target is the user and an example of the determination in a case in which the evaluation target is the user are not limited to the examples described in the foregoing (a-1) to (a-3).

(b) Example of Target Data Regarding Company, Party, Organization, or the Like

As target data regarding to a company or the like, for example, one or both of data indicating financial results of the company or the like and data indicating news related to the company or the like can be exemplified.

For example, in a case in which the target data includes the data indicating the financial results, the information processing apparatus according to the embodiment evaluates the company or the like by determining whether the financial results satisfy one or two or more set conditions (which are examples of the evaluation index) and setting a rating of the company or the like. Further, in a case in which the target data includes the data indicating the news related to the company or the like, the information processing apparatus according to the embodiment may evaluate the company or the like by determining whether content of the news is negative or positive and setting the rating of the company or the like. Here, a result obtained by setting the rating of the company or the like is equivalent to a result obtained by evaluating the company or the like.

Note that it is needless to say that an example of the target data in the case in which the evaluation target is a company, party, or organization and an example of the determination in a case in which the evaluation target is the company, party, or organization are not limited to the foregoing examples.

(c) Example of Target Data Regarding Object

For example, in a case in which an object of the evaluation target is an ore such as diamond or gold, for example, data in each stage from mining to processing of the ore can be exemplified as target data regarding the object.

For example, in a case in which the object of the evaluation target is an ore, for example, the following data can be exemplified as the target data regarding the object:

"data indicating an evaluation result of the object with a numerical value": an example of data equivalent to the above-described first data; and "raw data indicating an inspection record" at the time of evaluation inspection serving a basis of the determination of the evaluation: an example of data equivalent to the above-described second data.

The information processing apparatus according to the embodiment determines a worth of the ore, for example, by determining whether the data in each stage from the mining to the processing of the ore satisfies one or two or more set conditions (where are examples of the evaluation index). Here, the determination result of the worth of the ore is equivalent to a result obtained by evaluating the ore (which is an example of the objet). As one example, the information processing apparatus according to the embodiment determines the worth of the ore by comparing a numerical value specified on the basis of the target data regarding the object (which is an example of the target data) with one or two or more set predetermined thresholds, as in the case in which the target data described in the foregoing (a-1) is the data indicating the test result.

Further, for example, in a case in which the target data further includes the additional data indicating a state in which the object is inspected for evaluation or an environment in which the object is inspected for the evaluation, the information processing apparatus according to the embodiment can also determine the worth of the ore further on the basis of the additional data, as in the case in which the target data described in the foregoing (a-1) is the data indicating the test result.

As the additional data indicating the state in which the object is inspected for evaluation in the case in which the object of the evaluation target is an ore, for example, raw data in each stage from mining to processing of the ore can be exemplified. Further, as the additional data indicating the environment in which the object is inspected for the evaluation in the case in which the object of the evaluation target is the ore, for example, one or both of "positional information indicating the position of an evaluator who performs an inspection related to the evaluation" and "environmental information indicating an environment related to the evaluator" can be exemplified. The additional data indicating the environment in which the object is inspected for the evaluation is generated by, for example, a biological sensor or the like worn by the evaluator in the inspection related to the evaluation. Further, the additional data indicating the environment in which the object is inspected for the evaluation is associated with time data at which the inspection related to the evaluation is performed and is recorded on a recording medium such as a recording medium included in a server that manages data.

As an example of a process based on the additional data in the case in which the object of the evaluation target is the ore, the information processing apparatus according to the embodiment adjusts a numerical value specified on the basis of the target data regarding the object (which is an example of the target data) on the basis of the additional data, for example, as in the process described in the foregoing (i). Then, the information processing apparatus according to the embodiment determines the worth of the ore by comparing the adjusted numerical value with one or two or more set predetermined thresholds.

Further, as another example of the process based on the additional data in the case in which the object of the evaluation target is the ore, the information processing apparatus according to the embodiment further determines legitimacy of the determination result of the worth of the ore on the basis of the additional data, for example, as in the process described in the foregoing (ii).

Further, the information processing apparatus according to the embodiment can also perform both the process of adjusting the numerical value based on the additional data and the process related to the determination of the legitimacy of the determination result of the worth of the ore based on the additional data.

Note that it is needless to say that an example of the target data in the case in which the evaluation target is the object and an example of the determination in the case in which the evaluation target is the object are not limited to the foregoing examples.

The information processing apparatus according to the embodiment evaluates the evaluation target on the basis of the target data acquired from the blockchain data circulated in the peer-to-peer network, for example, as in the examples described in the foregoing (a) to (c).

Accordingly, the information processing apparatus according to the embodiment performs the evaluation process described above through the process related to the information processing method according to the embodiment, so that the evaluation of the evaluation target based on the target data regarding the evaluation target maintained on the network can be realized.

Here, since the target data is acquired from the blockchain data circulated on the peer-to-peer network, a possibility of the target data being altered is low. Accordingly, the information processing apparatus according to the embodiment can legitimately evaluate the evaluation target using the target data maintained on the network.

Further, the information processing apparatus according to the embodiment evaluates the evaluation target on the basis of the target data acquired from the blockchain data by the set evaluation criterion, as described above. Accordingly, by performing the foregoing evaluation process in each of the plurality of information processing apparatuses according to the embodiment which can access the peer-to-peer network, it is possible to realize an information processing system capable of realizing evaluation of the evaluation target by the criterion of each evaluator.

Note that the evaluation process is divided into the processes related to the information processing method according to the embodiment for convenience. Accordingly, in the processes related to the information processing method according to the embodiment, for example, the foregoing evaluation process can also be ascertained as two or more processes (in accordance with any dividing method).

[3] Application Example of Information Processing Method According to Embodiment Next, the processes related to the information processing method according to the embodiment will be described more specifically while describing use cases to which the information processing method according to the embodiment is applied.

Hereinafter, a case in which the target data is data regarding the test result of the user (which is an example of the target data regarding the user) and the information processing apparatus according to the embodiment evaluates the test result of the user who is the evaluation target will be described. Further, a case in which the target data is acquired from blockchain data circulated in an existing peer-to-peer network related to Bitcoin will be exemplified.

Note that use cases to which the information processing method according to the embodiment is applied are not limited to the foregoing examples. The information processing method according to the embodiment can be applied to, for example, any use case in which evaluation of an evaluation target, such as evaluation of a worth of an ore such as diamond or gold (which is an example of a case in which the target data is target data regarding the evaluation target), is performed using the target data.

Figure 2:
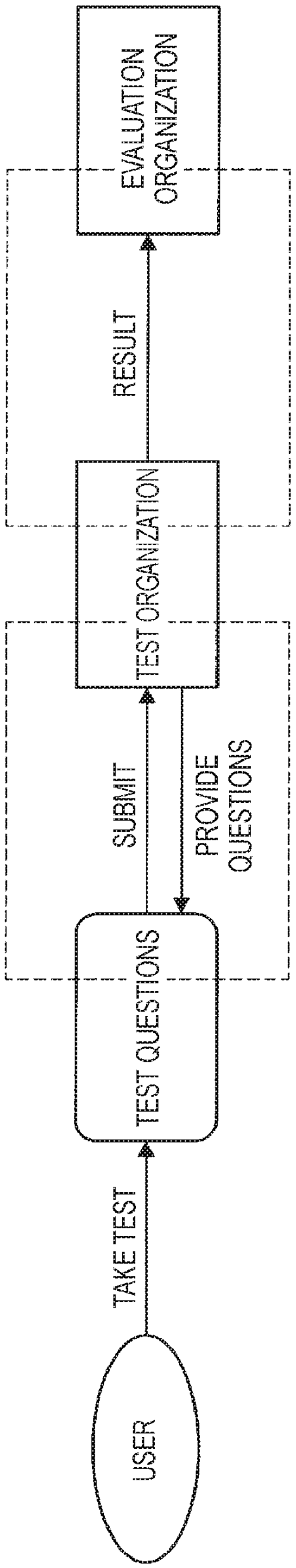
FIG. 2 is an explanatory diagram illustrating an example of a use case to which the information processing method according to the embodiment is applied.
Figure 4:
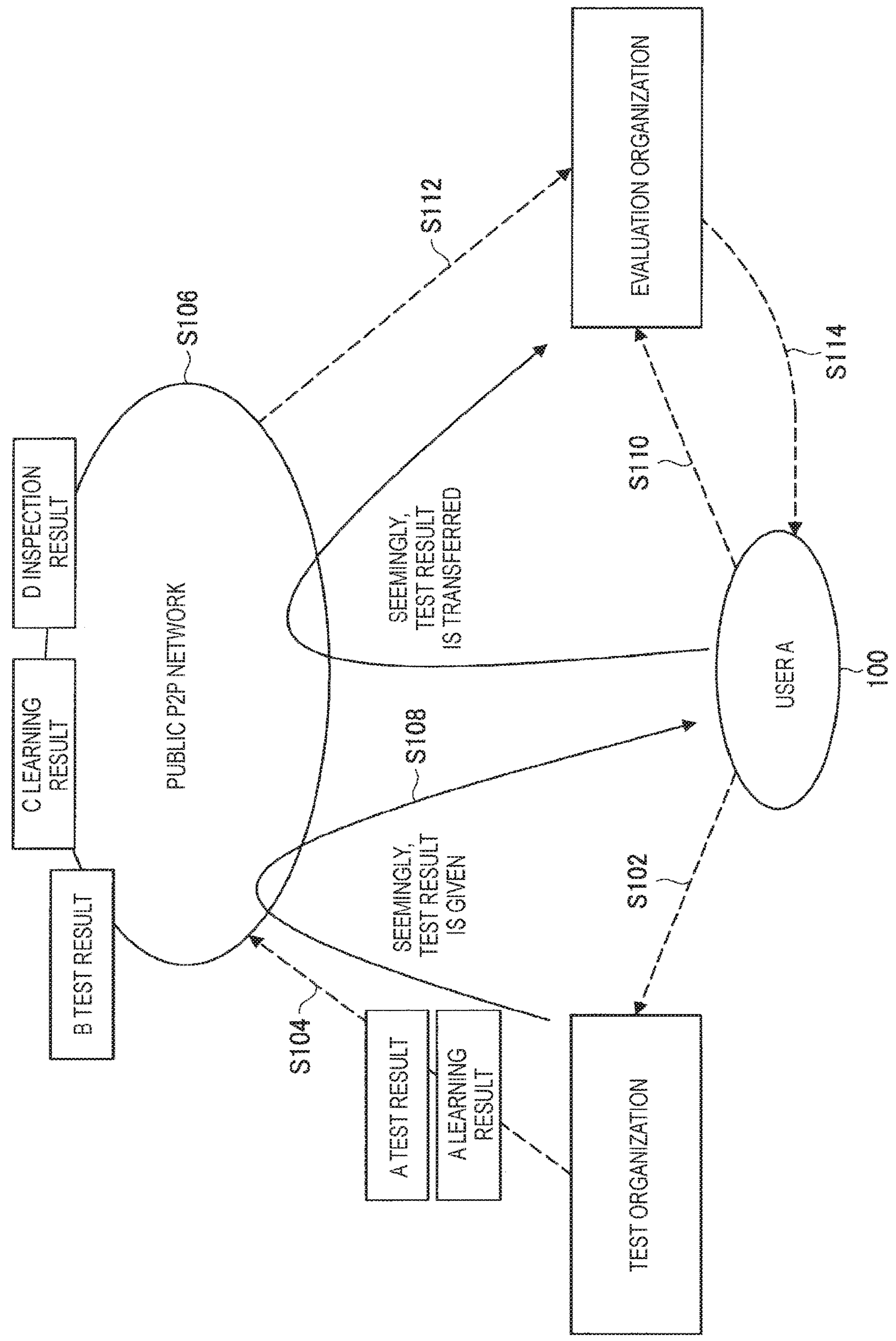
FIG. 4 is an explanatory diagram illustrating an example of a use case to which the information processing method according to the embodiment is applied.

FIG. 2 is an explanatory diagram illustrating an example of a use case to which the information processing method according to the embodiment is applied.

A test organization illustrated in FIG. 2 is an organization that provides test questions (or tasks) to each examinee (equivalent to a user). As the test organization, for example, an organization that performs a language test such as an English test or an organization that performs an entrance test for universities can be exemplified. Note that only one test organization is illustrated in FIG. 2, but there may be a plurality of test organizations. Further, only one examinee is illustrated in FIG. 2, but there may be a plurality of examinees.

When an examinee takes a test, a test result is typically maintained in a test organization.

Further, for example, the test organization can grant scores as an evaluation scores on the basis of test results. Note that the granting of the scores based on the test results may be performed by an evaluation organization.

The evaluation organization illustrated in FIG. 2 is an organization that evaluates a test result of the user who is an examinee. The evaluation organization evaluates the test result of the user, for example, by using the information processing apparatus according to the embodiment. In the evaluation organization, a result obtained by evaluating the test result of the user is utilized, for example, to determine pass or fail of an admission test or an employment entrance test or for health diagnosis. Note that only one evaluation organization is illustrated in FIG. 2, but there may be a plurality of evaluation organizations.

In a case in which an existing peer-to-peer network related to Bitcoin is used as the peer-to-peer network according to the embodiment, a test result is exchanged between the user and the test organization or the evaluation organization just as Bitcoin is exchanged between users.

FIG. 3 is an explanatory diagram illustrating an example of a use case to which the information processing method according to the embodiment is applied. FIG. 3 illustrates an example of data included in blockchain data circulated in the peer-to-peer network. Here, a transaction ID illustrated in FIG. 3 is exemplary. As the transaction ID, for example, a value subjected to base 58 encoding can be exemplified (the same applies below).

For example, the data illustrated in FIG. 3 remains on the blockchain data in a form in which the data is encrypted and anyone can browse the data. For example, a history of a state in which a user B takes a test or the user B submits a test result to the evaluation organization can be ascertained with reference to the data illustrated in FIG. 3.

FIG. 3 is an explanatory diagram illustrating the example of the use case to which the information processing method according to the embodiment is applied. Hereinafter, an example of the use case to which the information processing method according to the embodiment is applied will be described with reference to FIG. 2.

(0) Preparation Stage (S100 of FIG. 2)

Each of the user, the test organization, and the evaluation organization has a different secret key, generates a public key with each secret key, and generate an address from the public key. Hereinafter, the address of the user is referred to as a "U address," the address of the test organization is referred to as a "T address," and the address of the evaluation organization is referred to as an "E address."

The address is changed for each transaction. Therefore, for example, each address is suffixed for expression like a U0 address (which is an example of the address of the user) or a U1 address (which is an example of the address of the user) below.

As described above, in the peer-to-peer network according to the embodiment, a plurality of addresses can be managed with a wallet as in the structure of Bitcoin. Here, to further improve safety, the address is preferably changed for each transaction.

(1) Test Taken by User (S102 of FIG. 2)

For example, in a case in which a test is performed in accordance with an existing test scheme such as computer based test (CBT), answers of the user (examinee) to the test questions are generally collected in the server.

On the other hand, in a case in which the information processing method according to the embodiment is used, data with the following various kinds of content can be collected as the data (which is an example of the target data) regarding the test result of the user. Here, examples of the following data are examples of the data which can be collected in a case in which the user answers multiple-choice questions.

selected answers a time taken for answers the number of clicks of mouse at time of answers movement of mouse memo content on screen information acquired from captured image captured by the imaging device (for example, a motion of a visual line, a motion of a body, a change in an attitude)

information acquired by the biological sensor (for example, a heart rate, a amount of perspiration, a body temperature, a blood oxygen level, an electrocardiogram, a distance from an answer input device, an attitude, a temperature, an atmospheric pressure, humidity, and brightness).

The foregoing data based on the answers of the user are collected in, for example, an apparatus such as a server of the test organization and is subsequently transmitted to the peer-to-peer network according to the embodiment. Note that the foregoing data may be transmitted to the peer-to-peer network according to the embodiment without passing through the apparatus such as the server of the test organization.

(2) Transmission of Test Result to Peer-to-Peer Network (S104 of FIG. 2)

The apparatus such as the server of the test organization records the data (raw data) based on the answers of the user on a recording medium.

Further, the apparatus such as the server of the test organization transmits, for example, one or both of the data based on the answers of the user and data in which the data based on the answers of the user is shaped is transmitted to the peer-to-peer network according to the embodiment. As the shaped data, for examples, scores which are given on the basis of the data based on the answers of the user and serve as evaluation scores can be exemplified. The grating of the scores is equivalent to scoring by the test organization. In the apparatus such as the server of the test organization, for example scores are given in a case in which answers to all the test questions in a test can be obtained. Further, in the apparatus such as the server of the test organization, for example, scores may be given for each test question of a test. As a scale of the scores to be given (a scale of a scoring result), as described above, various scales such as scores of a single whole test and scores of each small question can be exemplified. The scale of the scores to be given may be decided in advance or may be decided depending on an application.

Here, the data based on the answers of the user and the shaped data are equivalent to the target data.

Note that which data is transmitted as the target data to the peer-to-peer network according to the embodiment can be changed by mutual agreement of the user and the test organization. For example, the target data to be transmitted to the peer-to-peer network according to the embodiment may be restricted by the user.

Further, the apparatus such as the server of the test organization may transmit the given scores (the scoring result of the test) to, for example, an apparatus carried by the user. The transmission of the given scores is performed via the peer-to-peer network, for example, as in remittance of Bitcoin on an existing peer-to-peer network related to Bitcoin. Further, the transmission of the given scores may be performed in such a manner that the apparatus such as the server of the test organization and the apparatus carried by the user perform communication directly (or via a network).

Figure 5:
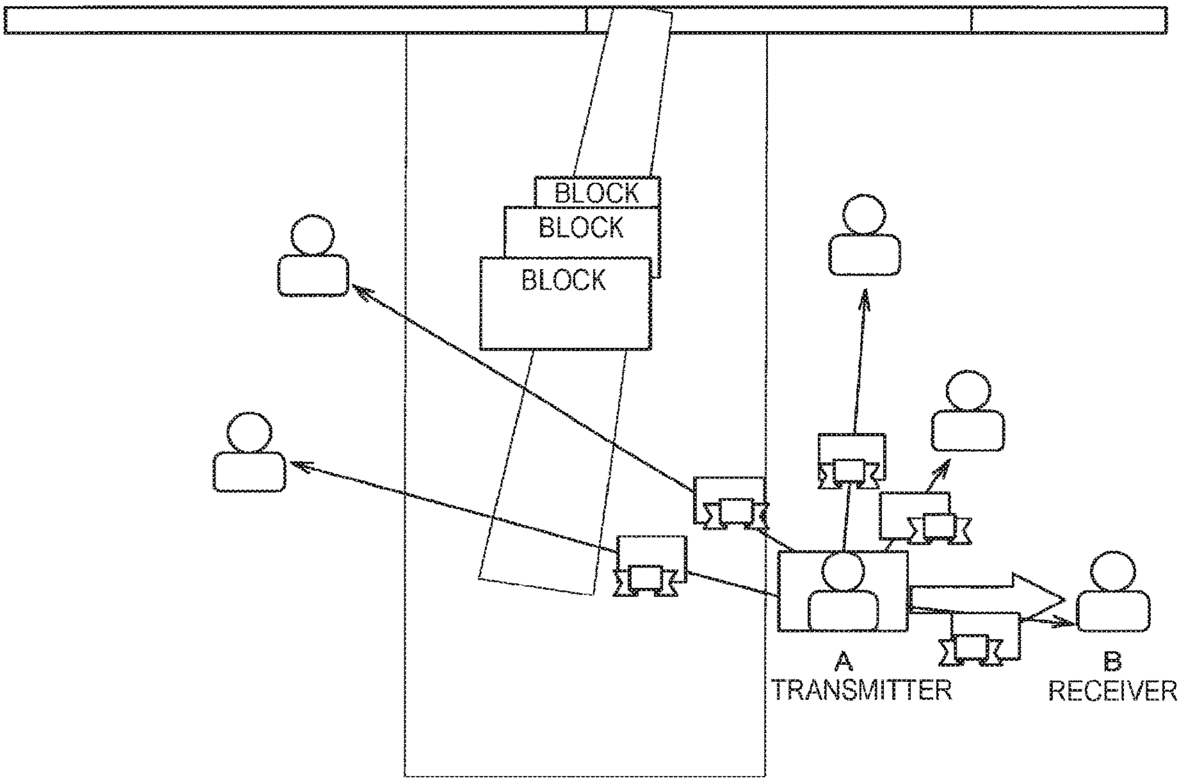
FIG. 5 is an explanatory diagram illustrating an example of a use case to which the information processing method according to the embodiment is applied.

FIG. 5 is an explanatory diagram illustrating an example of a use case to which the information processing method according to the embodiment is applied. FIG. 5 illustrates an overview of the transmission of scores from the apparatus such as the server of the test organization to the apparatus carried by the user.

A transmitter A illustrated in FIG. 5 is equivalent to the apparatus such as the server of the test organization and is equivalent to a remitter of Bitcoin in the existing peer-to-peer network related to Bitcoin. Further, a receiver B illustrated in FIG. 5 is equivalent to the apparatus carried by the user and corresponds to a recipient of Bitcoin in the existing peer-to-peer network related to Bitcoin.

(3) Circulation of Blockchain Data of Target Data (S106 of FIG. 2)

Figure 6:
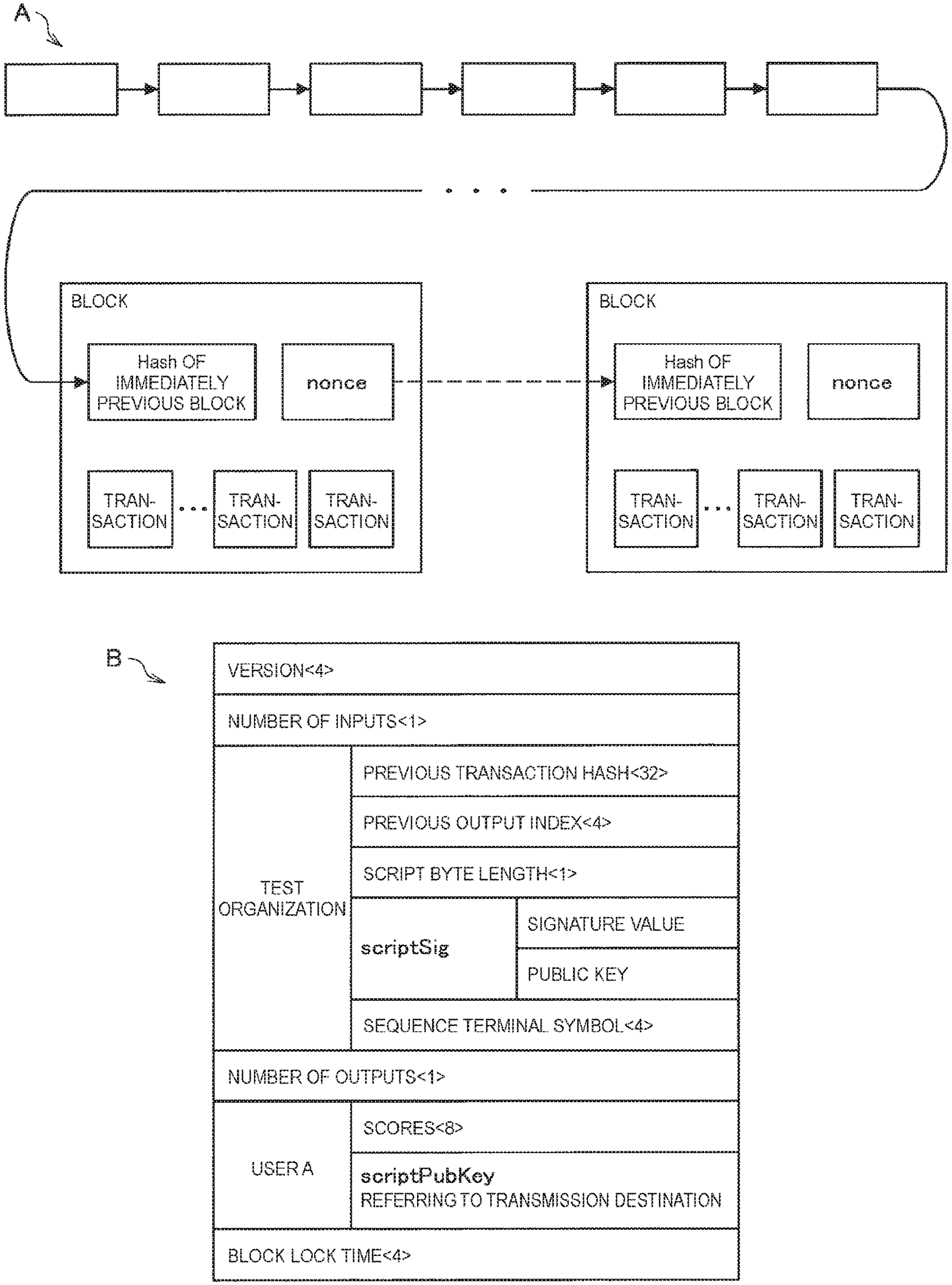
FIG. 6 is an explanatory diagram illustrating an example of a use case to which the information processing method according to the embodiment is applied.

FIG. 6 is an explanatory diagram illustrating an example of a use case to which the information processing method according to the embodiment is applied. A of FIG. 6 illustrates an overview of blockchain data in a case in which the peer-to-peer network according to the embodiment is the existing peer-to-peer network related to Bitcoin. Further, B of FIG. 6 illustrates an example of a transaction in the blockchain data and is equivalent to an example of the target data included in the blockchain data.

As illustrated in A of FIG. 6, in the blockchain data, a plurality of blocks are connected like chains. In one block, a plurality of transaction records are stored as transactions. Each transaction includes target data, for example, as illustrated in B of FIG. 6. Here, B of FIG. 6 illustrates transaction records in a case in which the test organization transmits data of scores which is a scoring result (which is an example of the target data) to the user A.

(4) Confirmation of Test Result by User (S108 of FIG. 2)

Figure 7:
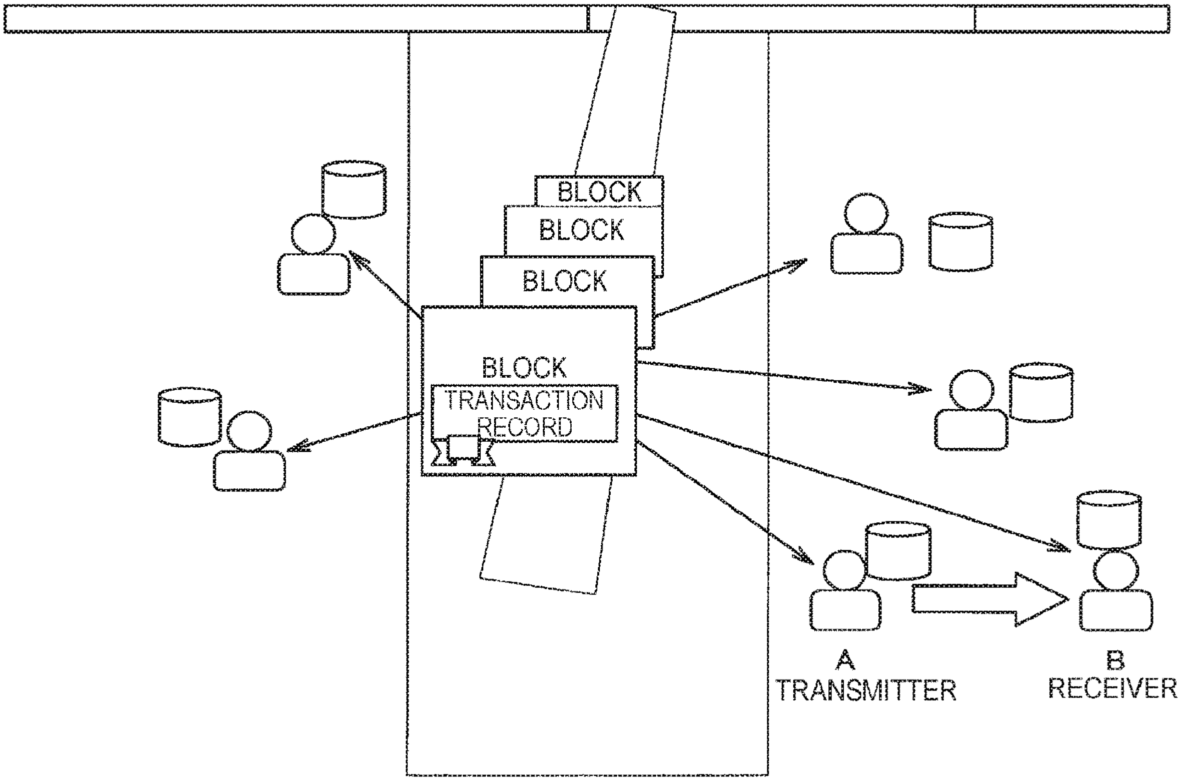
FIG. 7 is an explanatory diagram illustrating an example of a use case to which the information processing method according to the embodiment is applied.

FIG. 7 is an explanatory diagram illustrating an example of a use case to which the information processing method according to the embodiment is applied. FIG. 7 conceptually illustrates an example of the peer-to-peer network in which the blockchain data is circulated.

As described in the foregoing (3), the target data is circulated in accordance with the blockchain data, and thus a participant of the peer-to-peer network who can access the peer-to-peer network in which the blockchain data is circulated can acquire an encrypted transaction record including the target data, as illustrated in FIG. 7. However, a participant who does not have a secret key corresponding to the public key used for the encryption may not perform decryption.

Further, as described above, for example, transmission of the given scores is performed via the peer-to-peer network as in remittance of Bitcoin in the existing peer-to-peer network related to Bitcoin. Accordingly, the user who has a secret key corresponding to the public key used for the encryption can safely acquire the scores which are the scoring result of the test which the user took via the peer-to-peer network.

(5) Submission of Test Result by User (S110 of FIG. 2)

The target data corresponding to the test result of the user is circulated in the peer-to-peer network in a form in which the target data is included in the blockchain data. Therefore, the evaluation organization can acquire the test result of the user from the peer-to-peer network, and thus submission of the test result to the evaluation organization can be further simplified.

For example, when an English test is assumed, generally, official scores of the English test are maintained by the test organization and a certificate of a test result is issued by the test organization. On the other hand, in a case in which the information processing method according to the embodiment is used, official scores of the English test remain in the blockchain data in a form in which anybody can browse the official scores in the encrypted state (however, only a specific person can perform decryption).

For example, in a case in which a plurality of addresses are managed with a wallet of the user, a plurality of addresses related to a previous taken test are maintained. Here, whether the addresses are maintained for each test or are maintained for each question of the test or are reduced as small as possible depends on a security policy. Further, as a method of further improving safety, for example, a method of segmenting the addresses for each transaction can be exemplified.

FIG. 8 is an explanatory diagram illustrating an example of a use case to which the information processing method according to the embodiment is applied. FIG. 8 illustrates an example of data included in the blockchain data circulated in the peer-to-peer network as in FIG. 3.

Here, as illustrated in A of FIG. 8, a user side can use the plurality of addresses in a single test, As illustrated in A of FIG. 8, when the plurality of addresses are used, an advantageous effect of further improving safety is expected.

The example illustrated in FIG. 8 is an example in which the user uses the U3 address to submit data of the scores which is a test result (which is an example of the target data) to two evaluation organizations, an evaluation organization corresponding to an EA address and an evaluation organization corresponding to an EB address. Note that the example illustrated in FIG. 8 is an example in which the data of the scores is submitted as the data regarding the test result of the user (which is an example of the target data), but as described above, the data regarding the test result of the user can include data of various kinds of content such as a time necessary for answers or information acquired by the biological sensor.

Figure 9:
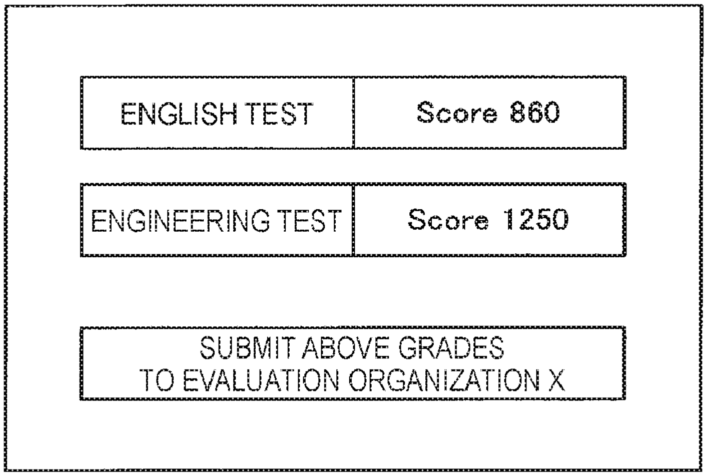
FIG. 9 is an explanatory diagram illustrating an example of a use case to which the information processing method according to the embodiment is applied.

FIG. 9 is an explanatory diagram illustrating an example of a use case to which the information processing method according to the embodiment is applied. FIG. 9 illustrates an example of a user interface (UI) related to the submission of the test result by the user.

For example, the management of a grade of the test of the user (which is equivalent to a test result) and the submission of the grade to the evaluation organization are realized on one screen by using the UI illustrated in FIG. 9. Note that it is needless to say that an example of a UI related to the management of the grade of the user according to the embodiment is not limited to the example illustrated in FIG. 9.

(6) Evaluation of Test Result of User by Evaluation Organization (S112 of FIG. 2)

FIG. 10 is an explanatory diagram illustrating an example of a use case to which the information processing method according to the embodiment is applied. FIG. 10 illustrates an example of data included in the blockchain data circulated in the peer-to-peer network as in FIG. 3. Hereinafter, an overview of evaluation (an overview of evaluation through the evaluation process in the information processing apparatus according to the embodiment) in the evaluation organization will be described exemplifying data illustrated in FIG. 10.

For example, a contents ID associated with a transaction ID illustrated in FIG. 10 uniquely indicates a single whole test or Question 1 in the test. The contents ID can be said to be an ID indicating the target data.

A scale of the contents necessary in the evaluation organization (content indicated by the target data) can be different. As the scale of the contents necessary in the evaluation organization, for example, various scales such as scores of a single test (final evaluation points) or each question (raw score) can be exemplified.

As described above, in a case in which the target data is data regarding a test result of the user, one or both of the first data in which the test result of the user is indicated by a numerical value and the second data in which the test result of the user is indicated by a value other than the numerical value can be exemplified as the target data. Further, as described above, in a case in which the target data is data regarding the test result of the user, the target data may further include the third data indicating a state in which the user takes a test or an environment in which the user takes the test. In the example illustrated in FIG. 10, for example, "scores of questions" is equivalent to the first data. Further, in the example illustrated in FIG. 10, for example, "answer content of questions" and "correct or incorrect answers to the questions" is equivalent to the second data. Further, in the example illustrated in FIG. 10, for example, "an answer time of questions," "a motion of a visual line of an examinee," "a change in an attitude of the examinee," "a heart rate or a amount of perspiration of the examinee," "an input speed of a keyboard," "a motion of a pointer," and "a situation of another application" are equivalent to the third data. Further, as described above, one or both of "positional information of the examinee" and "environmental information around the examinee (data indicating a temperature, an atmospheric pressure, humidity, brightness, or the like)" may be included as the third data.

Here, for example, a presenting order of the questions or an answering order of the user can be determined from an order of transactions recorded on a blockchain. Further, depending on the format of data recorded on the blockchain, the presenting order of the questions or the answering order of the user may not be determined from the order of the transactions recorded on the blockchain in some cases. In a case in which the presenting order of the questions or the like may not be determined from the order of the transactions, information indicating one or both of the presenting order of the questions and the answering order of the user may be included in the second data or the second data.

For example, the evaluation organization acquires data indicating the raw scores from the blockchain data and calculates independent scores of the evaluation organization (which is an example of the evaluation process based on the above-described first data) for evaluation. Note that the evaluation organization can also perform evaluation through another process such as an evaluation process based on the above-described second data or an evaluation process based on the above-described third data, as described above.

Here, it is guaranteed that the data acquired from the blockchain data is safe and is not altered. Accordingly, by performing the evaluation on the basis of the target data acquired from the blockchain data, for example, "exchange of only data regarding the test result of the user (which is an example of the target data) and independent evaluation by each evaluation organization" can be realized.

FIG. 11 is an explanatory diagram illustrating an example of a use case to which the information processing method according to the embodiment is applied. FIG. 11 illustrates an example of a case in which another evaluation is performed on the same test result by another evaluation organization.

In a case in which the test result illustrated in A of FIG. 11 is evaluated by each of evaluation organizations X and Y, the evaluation result may differ, as illustrated in B of FIG. 11.

Here, B of FIG. 11 illustrates an example in which the raw scores are given by the evaluation organization X. Further, B of FIG. 11 illustrates an example in which the evaluation organization Y performs addition of scores (which is example of adjustment of the scores) in accordance with an answer time or the like. As a specific example, in the example illustrated in B of FIG. 11, the evaluation organization Y performs the addition of scores, as indicated by P, as the answer time sis shorter. Further, in the example illustrated in B of FIG. 11, the evaluation organization Y performs the addition, as indicated by Q, in accordance with partial scores although the answer time is long.

(7) Delivery of Evaluation Result to User (S114 of FIG. 2)

When the test result is submitted by the user, as described in the foregoing (5), the evaluation organization can consider that the user requests evaluation. Here, a specific example of the request of the evaluation by the user is equivalent to, for example, application to an entrance test to a school or an employment entrance test of a company.

Accordingly, the evaluation organization delivers a result of the evaluation of the test result (pass or fail of the admission test) of the user by the evaluation organization described in the foregoing (6) to the user.

Here, as a method of delivering the result of the evaluation to the user, for example, any method capable of delivering the result of the evaluation of the user to the user, such as "delivery via a peer-to-peer network in accordance with the same method as the remittance of Bitcoin in the existing peer-to-peer network related to Bitcoin" "delivery through direct communication (or via a network) among a server of the evaluation organization, an apparatus such as the information processing apparatus according to the embodiment, and the apparatus carried by the user", or "delivery by post," can be exemplified.

[4] Example of Advantageous Effect Provided Using Information Processing Method According to Embodiment When the information processing apparatus according to the embodiment performs the evaluation process related to the information processing method according to the embodiment, for example, the following advantageous effects can be obtained. Note that it is needless to say that advantageous effects obtained using the information processing method according to the embodiment are not limited to the following advantageous effects.

For example, in a case in which a test is performed in accordance with an existing test scheme such as CBT, a test organization and an evaluation organization are identical in many cases. Further, in a case in which a test is performed in accordance with an existing test scheme, a test made by a specific evaluation organization can be provided by another test organization. When the information processing method according to the embodiment is used, a test result submitted from a user to the test organization is completely separated from a test result evaluated by the evaluation organization. Accordingly, when the information processing method according to the embodiment is used, the evaluation organization can flexibly evaluate the test result of the user, for example, by scoring the test result of the user in accordance with an independent criterion even in a case in which the test organization and the evaluation organization are different.

In a case in which the information processing method according to the embodiment is used, the target data is acquired from the blockchain data circulated in the peer-to-peer network. Here, the target data is encrypted on the blockchain data. Therefore, anyone who can access the peer-to-peer network can touch the target data, but the target data is not decrypted when there is no secret key corresponding to the encrypted target data. Accordingly, in the case in which the information processing method according to the embodiment is used, the confidentiality of the content indicated by the target data can be sufficiently guaranteed while setting the target data as open data which is data which can be touched by anyone.

For example, in a case in which a test is performed in accordance with an existing test scheme such as CBT, illegality can be examined by the test organization in a case in which there is the illegality in the test. In the case in which the information processing method according to the embodiment is used, the target data is maintained as open data on the peer-to-peer network. Therefore, the evaluation organization can also evaluate legitimacy of the test while evaluating a test result. For example, in a case in which a certain examinee cheats and answers in a short time, there is a possibility of illegality being determined by the evaluation organization by statistically evaluating from another viewpoint even when the test organization may not determine the illegality when the information processing method according to the embodiment is used.

The use case in which the test result of the user who is the evaluation target has been exemplified above as the use case to which the information processing method according to the embodiment is applied. However, as described above, a use case to which the information processing method according to the embodiment can be applied is not limited to the foregoing example. For example, evaluation of a heath state of a user who is an evaluation target can be realized with the same structure as the structure evaluating the test result of the user, as described above. For example, the evaluation organization which outputs a second opinion can output the second opinion by acquiring data regarding an inspection result of health diagnosis of a user who is the evaluation target (for example raw data indicating a measured inspection record; so-called healthcare data) from the blockchain data circulated in the peer-to-peer network and evaluating the data. In this example, for example, “a result of the health diagnosis” evaluated step by step such as 10 steps from “1” to “10” is equivalent to the first data. Further, in this example, for example, “the raw data indicating the inspection record” is equivalent to the second data. Further, for example, while a medical examinee takes a health diagnosis, a device continuously measuring biological information of the medical examinee or environmental surrounding information may be worn by the medical examinee, and one or both of biological information indicating a heart rate, a amount of perspiration, a body temperature, a blood oxygen level, an electrocardiogram or an attitude and the surrounding environmental information indicating a distance from a medical examination input device, a temperature, an atmospheric pressure, humidity, and brightness may be recorded on a recording medium along with time information. In a case in which the biological information or the like is recorded, the “biological information” and the “surrounding environmental information” of the medical examinee are equivalent to the additional data.

(Information Processing Apparatus According to the Present Embodiment)

An example of a configuration of the information processing apparatus according to the present embodiment which can perform the above-described processing associated with the information processing method according to the present embodiment will be described next.

Figure 12:
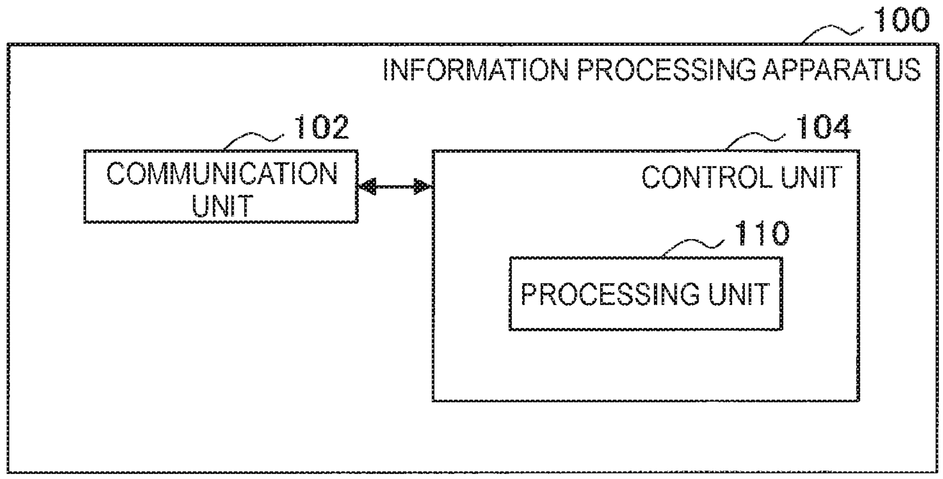
FIG. 12 is a block diagram illustrating an example of a configuration of an information processing apparatus according to the present embodiment.

FIG. 12 is a block diagram illustrating an example of the configuration of the information processing apparatus 100 according to the present embodiment. The information processing apparatus 100 includes, for example, a communication unit 102 and a control unit 104.

Further, the information processing apparatus 100 may include, for example, a read only memory (ROM, which is not illustrated), a random access memory (RAM, which is not illustrated), a storage unit (which is not illustrated), an operation unit (which is not illustrated) which can be operated by the user, a display unit (which is not illustrated) which displays various screens on a display screen, or the like. The information processing apparatus 100, for example, connects the above-described respective components using a bus which is a data transmission path.

The ROM (which is not illustrated) stores control data such as a program and an operation parameter to be used by the control unit 104. The RAM (which is not illustrated) temporarily stores a program to be executed by the control unit 104.

The storage unit (which is not illustrated) is storage means included in the information processing apparatus 100 and stores, for example, data related to the information processing method according to the embodiment, such as a cryptographic key corresponding to an evaluation target or a table in which content which may be indicated by the second data matches numerical values, or various kinds of data such as various applications. Here, examples of the storage unit (which is not illustrated) can include, for example, a magnetic recording medium such as a hard disk, and a nonvolatile memory such as a flash memory. Further, the storage unit (which is not illustrated) may be detachable from the information processing apparatus 100.

Examples of the operation unit (which is not illustrated) can include an operation input device which will be described later. Further, examples of the display unit (which is not illustrated) can include a display device which will be described later.

[Hardware Configuration Example of Information Processing Apparatus 100]

Figure 13:
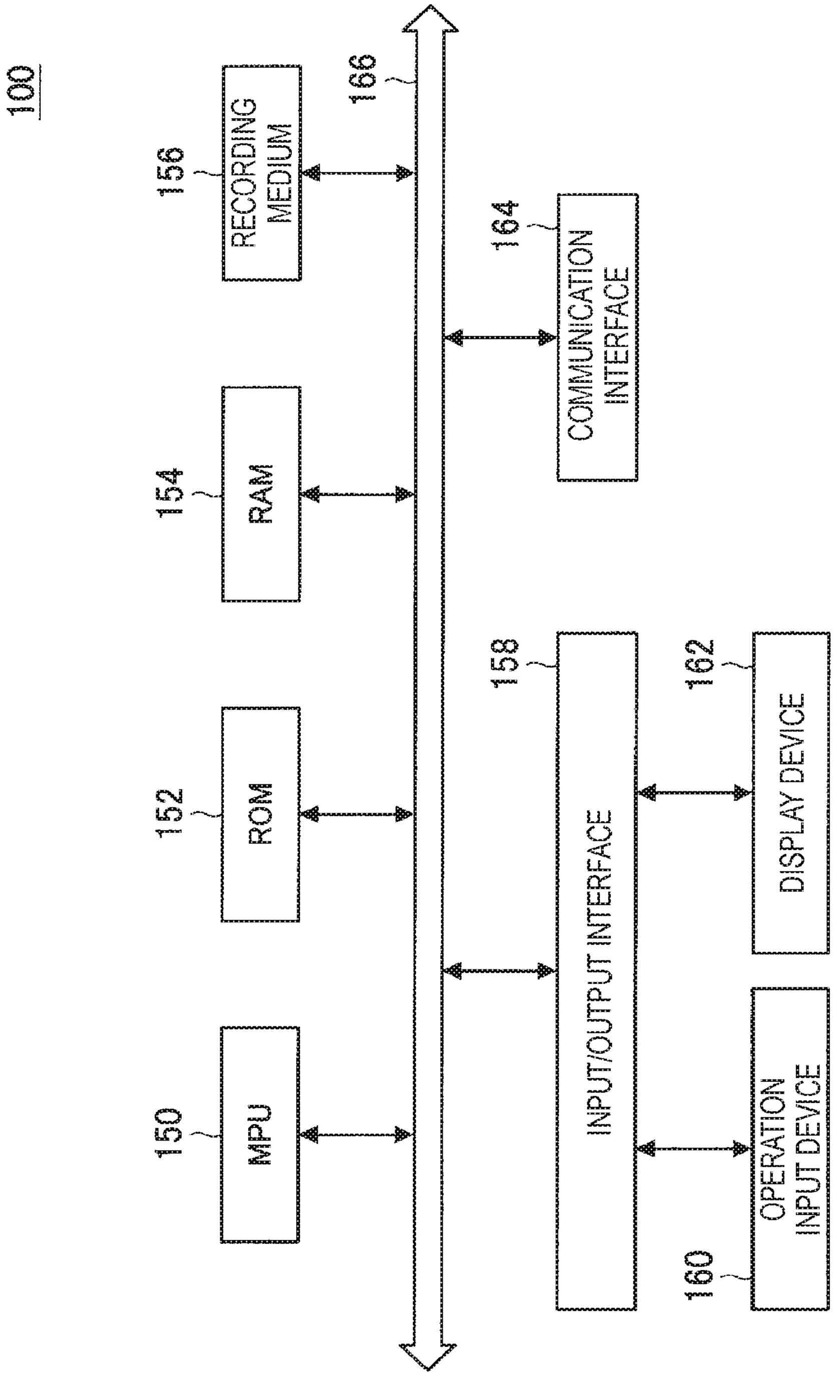
FIG. 13 is an explanatory diagram illustrating an example of a hardware configuration of the information processing apparatus according to the present embodiment.

FIG. 13 is an explanatory diagram illustrating an example of a hardware configuration of the information processing apparatus 100 according to the present embodiment. The information processing apparatus 100 includes, for example, an MPU 150, a ROM 152, a RAM 154, a recording medium 156, an input/output interface 158, an operation input device 160, a display device 162 and a communication interface 164. Further, the information processing apparatus 100 connects the respective components using a bus 166 which is a data transmission path.

The MPU 150 includes, for example, one or more processors including an arithmetic circuit such as an MPU, various kinds of processing circuits, or the like, and functions as a control unit 104 which controls the whole of the information processing apparatus 100. Further, the MPU 150 plays a role of, for example, a processing unit 110 which will be described later, in the information processing apparatus 100. Note that the processing unit 110 may include a dedicated (or general-purpose) circuit (such as, for example, a processor separate from the MPU 150) which can realize processing of the processing unit 110.

The ROM 152 stores control data such as a program and an operation parameter, or the like, to be used by the MPU 150. The RAM 154 temporarily stores a program, or the like, to be executed by the MPU 150.

The recording medium 156 functions as a storage unit (which is not illustrated) and, for example, stores data associated with the information processing method according to the present embodiment such as a cryptographic key corresponding to the evaluation target and various kinds of data such as various kinds of application. Here, examples of the recording medium 156 can include, for example, a magnetic recording medium such as a hard disk, and a nonvolatile memory such as a flash memory. Further, the recording medium 156 may be detachable from the information processing apparatus 100.

The input/output interface 158, for example, connects the operation input device 160 and the display device 162. The operation input device 160 functions as an operation unit (which is not illustrated), and the display device 162 functions as a display unit (which is not illustrated). Here, examples of the input/output interface 158 can include, for example, a universal serial bus (USB) terminal, a digital visual interface (DVI) terminal, a high-definition multimedia interface (HDMI) (registered trademark) terminal and various kinds of processing circuits.

Further, the operation input device 160, for example, is provided on the information processing apparatus 100, and is connected to the input/output interface 158 inside the information processing apparatus 100. Examples of the operation input device 160 can include, for example, a button, a direction key, a rotary selector such as a jog dial or combination thereof.

Further, the display device 162 is, for example, provided on the information processing apparatus 100 and is connected to the input/output interface 158 inside the information processing apparatus 100. Examples of the display device 162 can include, for example, a liquid crystal display, an organic electro-luminescence (EL) display, and an organic light emitting diode (OLED) display.

Note that it goes without saying that the input/output interface 158 can be connected to an external device such as an external operation input device (such as, for example, a keyboard and a mouse) and an external display device of the information processing apparatus 100. Further, the display device 162 may be a device which can perform display and allow user operation, such as, for example, a touch panel.

The communication interface 164 is communication means included in the information processing apparatus 100 and functions as the communication unit 102 that performs wireless or wired communication with an external apparatus that forms the peer-to-peer network according to the embodiment. Further, the communication interface 164 may have, for example, a function of performing wired or wireless communication with any external apparatus such as a server via any network (or directly). Here, examples of the communication interface 164 can include, for example, a communication antenna and a radio frequency (RF) circuit (wireless communication), an IEEE802.15.1 port and a transmission/reception circuit (wireless communication), an IEEE802.11 port and a transmission/reception circuit (wireless communication) and a local area network (LAN) terminal and a transmission/reception circuit (wired communication).

The information processing apparatus 100 performs the processing associated with the information processing method according to the present embodiment according to the configuration illustrated in, for example FIG. 8. Note that the hardware configuration of the information processing apparatus 100 according to the present embodiment is not limited to the configuration illustrated in FIG. 13.

For example, in the case where the information processing apparatus 100 performs communication with an external apparatus, or the like, via a connected external communication device, the information processing apparatus 100 does not have to include the communication interface 164. Further, the communication interface 164 may have a configuration so as to be able to perform communication with one or more external apparatuses, or the like, using a plurality of communication schemes.

Further, the information processing apparatus 100 can, for example, employ a configuration which does not include the recording medium 156, the operation input device 160 and the display device 162.

Further, for example, part or all of the components illustrated in FIG. 13 (or components according to a modified example) may be implemented with one or more integrated circuits (ICs).

Referring back to FIG. 12, the example of the configuration of the information processing apparatus 100 will be described. The communication unit 102 is communication means included in the information processing apparatus 100 and performs wireless or wired communication with an external apparatus that forms the peer-to-peer network according to the embodiment. Further, the communication unit 102 may have, for example, a function of performing wired or wireless communication with any external apparatus such as a server via any network (or directly). Further, the communication of the communication unit 102 is controlled by, for example, the control unit 104.

Here, while examples of the communication unit 102 can include, for example, a communication antenna and an RF circuit, and a LAN terminal and a transmission/reception circuit, the configuration of the communication unit 102 is not limited to the above-described examples. For example, the communication unit 102 can employ a configuration supporting an arbitrary standard which enables communication, such as a USB terminal and a transmission/reception circuit, and an arbitrary configuration which enables communication with external apparatuses via a network. Further, the communication unit 102 may have a configuration so as to be able to perform communication with one or more external apparatuses using a plurality of communication schemes.

The control unit 104, which includes, for example, an MPU, plays a role of controlling the whole of the information processing apparatus 100. Further, the control unit 104 includes, for example, a processing unit 110 and plays a role of leading the processing associated with the information processing method according to the present embodiment.

The processing unit 110 has a role of leading the evaluation process related to the information processing method according to the embodiment and evaluates the evaluation target on the basis of the target data acquired from the blockchain data circulated in the peer-to-peer network.

For example, the processing unit 110 acquires the target data corresponding to the evaluation target from the blockchain data by performing decryption with a cryptographic key corresponding to the evaluation target (for example, a secret key corresponding to a public key used to encrypt the target data). Further, the processing unit 110 evaluates the evaluation target, for example, as in the examples described in the foregoing (a) to (c).

The control unit 104 includes, for example, the processing unit 110 and thus plays a role of leading the process related to the information processing method according to the embodiment (for example, the evaluation process according to the embodiment).

The information processing apparatus 100 has, for example, the configuration illustrated in FIG. 12, and thus performs the process related to the information processing method according to the embodiment (the evaluation process according to the embodiment).

Accordingly, the information processing apparatus 100 has, for example, the configuration illustrated in FIG. 12, and thus can realize the evaluation of the evaluation target based on the target data related to the evaluation target maintained on the network.

Further, the information processing apparatus 100 can provide an effect provided by the processing associated with the information processing method according to the present embodiment as described above being performed according to the configuration illustrated in, for example, FIG. 12.

Note that the configuration of the information processing apparatus according to the present embodiment is not limited to the configuration illustrated in FIG. 12.

For example, the information processing apparatus according to the present embodiment can include the processing unit 110 illustrated in FIG. 12 separately from the control unit 104 (for example, implements the processing unit 110 with a separate processing circuit).

Further, as described above, the evaluation process according to the embodiment is a process in which the process related to the information processing method according to the embodiment is defined for convenience. Accordingly, the configuration for realizing the process related to the information processing method according to the embodiment is not limited to the configuration illustrated in FIG. 12 and can be a configuration in accordance with the a method of dividing the process related to the information processing method according to the embodiment.

Further, for example, in the case where communication is performed with an external apparatus via an external communication device having functions and a configuration similar to those of the communication unit 102, the information processing apparatus according to the present embodiment does not have to include the communication unit 102.

The information processing apparatus has been described above according to the embodiment, but the embodiment is not limited to this form. The embodiment can be applied to, for example, various apparatuses such as computers such as a personal computer (PC) and a server capable of performing the process related to the information processing method according to the embodiment. Further, the embodiment can be applied to, for example, a processing IC which can be embedded in the foregoing apparatus.

Further, the information processing apparatus according to the embodiment may be applied to a processing system assumed to be connected to a network (or communication between apparatuses) such as clouding computing. As an example of the processing system that performs the process related to the information processing method according to the embodiment, for example, "a system in which one apparatus included in the processing system performs a partial process of the evaluation process related to the information processing method according to the embodiment and another apparatus included in the processing system performs a process other than the partial process of the evaluation process related to the information processing method according to the embodiment" can be exemplified.

(Program According to the Present Embodiment)

When a program causing a computer to function as the information processing apparatus according to the embodiment (for example, a program capable of executing a process related to the information processing method according to the embodiment, such as an evaluation process according to the embodiment) is executed by a processor or the like on the computer, it is possible to realize evaluation of an evaluation target based on the target data regarding the evaluation target maintained on a network.

Moreover, when a program that causes a computer to function as the information processing apparatus according to the present embodiment is executed by a processor or the like in the computer, it is possible to provide an effect provided by the processing related to the information processing method according to the present embodiment described above.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, it has been illustrated above that a program (computer program) that causes a computer to function as the information processing apparatus according to the present embodiment is provided, but the present embodiment can further provide a recording medium in which the above-described program is stored together.

The above-described configurations express examples of the present embodiment and, of course, pertain to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a processing unit configured to evaluate an evaluation target on a basis of target data regarding the evaluation target acquired from blockchain data circulated on a peer-to-peer network.

(2)

The information processing apparatus according to (1), in which the processing unit acquires the target data corresponding to the evaluation target from the blockchain data by performing decryption with a cryptographic key corresponding to the evaluation target.

(3)

The information processing apparatus according to (1) or (2), in which the processing unit evaluates the evaluation target in accordance with a set evaluation index corresponding to the evaluation target.

(4)

The information processing apparatus according to any one of (1) to (3), in which the evaluation target is a user, and the processing unit evaluates the user on the basis of the target data.

(5)

The information processing apparatus according to (4), in which the target data is data regarding a test result of the user, and the processing unit evaluates the test result of the user.

(6)

The information processing apparatus according to (5), in which the processing unit evaluates the test result of the user by comparing a numerical value specified on the basis of the target data with one or two or more set predetermined thresholds.

(7)

The information processing apparatus according to (6), in which, in a case in which the target data includes first data in which the test result of the user is indicated by a numerical value, the numerical value specified on the basis of the target data is specified on a basis of the numerical value indicated by the first data.

(8)

The information processing apparatus according to (6) or (7), in which, in a case in which the target data includes second data in which the test result of the user is indicated by a value other than a numerical value, the numerical value specified on the basis of the target data is specified on a basis of a numerical value acquired on a basis of the second data.

(9)

The information processing apparatus according to any one of (6) to (8), in which, in a case in which the target data further includes third data indicating a state in which the user takes a test or an environment in which the user takes the test, the processing unit evaluates the test result of the user further on a basis of the third data.

(10)

The information processing apparatus according to (9), in which, on the basis of the third data, the processing unit adjusts the numerical value specified on the basis of the target data, and the processing unit evaluates the test result of the user by comparing the adjusted numerical value with the one or more or more predetermined threshold values.

(11)

The information processing apparatus according to (9) or (10), in which the processing unit further determines legitimacy of the test result on the basis of the third data.

(12)

The information processing apparatus according to any one of (1) to (11), in which the processing unit evaluates the evaluation target on a basis of a plurality of pieces of the target data corresponding to the evaluation target.

(13)

The information processing apparatus according to (4), in which the target data is data regarding an inspection result of the user, and the processing unit evaluates the inspection result of the user by comparing the numerical value specified on the basis of the target data with one or two or more set predetermined thresholds.

(14)

The information processing apparatus according to (13), in which, in a case in which the target data further includes additional data indicating a state in which the user undergoes an inspection or an environment in which the user undergoes the inspection, the processing unit evaluates the inspection result of the user further on a basis of the additional data.

(15)

The information processing apparatus according to any one of (1) to (3), in which the evaluation target is an object, and the processing unit evaluates the object on the basis of the target data.

(16)

The information processing apparatus according to (15), in which the target data is data regarding an evaluation result of the object, and the processing unit evaluates the evaluation result of the object by comparing the numerical value specified on the basis of the target data with one or two or more set predetermined thresholds.

(17)

The information processing apparatus according to (16), in which, in a case in which the target data further includes additional data indicating a state in which the object undergoes an inspection for evaluation or an environment in which the object undergoes an inspection for the evaluation, the processing unit evaluates the inspection result of the object further on a basis of the additional data.

(18)

An information processing method to be performed by an information processing apparatus, the information processing method including:

a step of evaluating an evaluation target on a basis of target data regarding the evaluation target acquired from blockchain data circulated on a peer-to-peer network.

(19)

A program causing a computer to execute a function of evaluating an evaluation target on a basis of target data regarding the evaluation target acquired from blockchain data circulated on a peer-to-peer network.

REFERENCE SIGNS LIST

100 information processing apparatus
102 communication unit
104 control unit

110 processing unit

The invention claimed is:

1. An information processing apparatus comprising:

processing circuitry configured to:

retrieve, from a peer-to-peer network circulating blockchain data and using an address generated from a public key, an encrypted test score of a user, the encrypted test score included within a plurality of transactions linked through one or more blocks of data, the public key being generated from a secret key, the one or more blocks of data being designated by the address, decrypt the encrypted test score using a cryptographic key, and calculate an evaluation score of the user based on the decrypted test score, wherein the address is used to identify the plurality of transactions to retrieve the encrypted test score, and wherein the one or more blocks of data designated by the address are not decrypted where there is no cryptographic key corresponding to the public key.

2. The information processing apparatus according to claim 1, wherein the processing circuitry is configured to calculate the evaluation score of the user in accordance with a set evaluation index corresponding to the user.

3. The information processing apparatus according to claim 1, wherein the processing circuitry is configured to calculate the evaluation score of the user by comparing a numerical value specified on the basis of the decrypted test score with one or two or more set predetermined thresholds.

4. The information processing apparatus according to claim 3, wherein, in a case in which the decrypted test score includes first data in which the decrypted test score of the user is indicated by a numerical value, the numerical value specified on the basis of the decrypted test score is specified on a basis of the numerical value indicated by the first data.

5. The information processing apparatus according to claim 3, wherein, in a case in which the decrypted test score includes second data in which the decrypted test score of the user is indicated by a value other than a numerical value, the numerical value specified on the basis of the decrypted test score is specified on a basis of a numerical value acquired on a basis of the second data.

6. The information processing apparatus according to claim 3, wherein, in a case in which the decrypted test score further includes third data indicating a state in which the user takes a test or an environment in which the user takes the test, the processing circuitry is further configured to calculate the evaluation score on a basis of the third data.

7. The information processing apparatus according to claim 6, wherein, on the basis of the third data, the processing circuitry adjusts the numerical value specified on the basis of the decrypted test score, and the processing circuitry is further configured to calculate the evaluation score of the user by comparing the adjusted numerical value with the one or more or more predetermined threshold values.

8. The information processing apparatus according to claim 6, wherein the processing circuitry is further configured to determine a legitimacy of the decrypted test score on the basis of the third data.

9. The information processing apparatus according to claim 1, wherein the processing circuitry is further configured to calculate the evaluation score of the user on a basis of a plurality of pieces of the decrypted test score corresponding to the user.

10. An information processing method to be performed by an information processing apparatus, the information processing method comprising:

retrieving, from a peer-to-peer network circulating blockchain data and using an address generated from a public key, an encrypted test score of a user, the encrypted test score included within a plurality of transactions linked through one or more blocks of data, the public key being generated from a secret key, the one or more blocks of data being designated by the address;

decrypting the encrypted test score using a cryptographic key; and calculating an evaluation score of the user based on the decrypted test score, wherein the address is used to identify the plurality of transactions to retrieve the encrypted test score;

wherein the one or more blocks of data designated by the address are not decrypted where there is no cryptographic key corresponding to the public key.

11. A non-transitory computer readable medium having instructions stored therein, which when executed by a processor in a computer causes the processor to execute a method comprising:

retrieving, from a peer-to-peer network circulating blockchain data and using an address generated from a public key, an encrypted test score of a user, the encrypted test score included within a plurality of transactions linked through one or more blocks of data, the public key being generated from a secret key, the one or more blocks of data being designated by the address;

decrypting the encrypted test score using a cryptographic key; and calculating an evaluation score of the user based on the decrypted test score, wherein the address is used to identify the plurality of transactions to retrieve the encrypted test score, and wherein the one or more blocks of data designated by the address are not decrypted where there is no cryptographic key corresponding to the public key.

* * * * *